(12) United States Patent
Köhler et al.

(10) Patent No.: US 7,112,971 B2
(45) Date of Patent: Sep. 26, 2006

(54) METHOD AND APPARATUS FOR DETERMINING THE MOISTURE CONTENT OF A MATERIAL

(75) Inventors: Kurt Köhler, Ettlingen (DE); Robin Fundinger, Karlsbad (DE)

(73) Assignee: Imko Intelligente Micromodule Köhler GmbH, Ettlingen (DE)

( * ) Notice: Subject to any disclaimer, the term of this patent is extended or adjusted under 35 U.S.C. 154(b) by 57 days.

(21) Appl. No.: 10/942,691

(22) Filed: Sep. 16, 2004

(65) Prior Publication Data
US 2005/0073321 A1  Apr. 7, 2005

(30) Foreign Application Priority Data
Oct. 2, 2003  (DE) ................................ 103 45 911

(51) Int. Cl.
*G01R 27/32*  (2006.01)

(52) U.S. Cl. ...................... 324/643; 324/640; 324/642; 324/637

(58) Field of Classification Search ................ 324/640, 324/533–534, 637, 642–643

See application file for complete search history.

(56) References Cited

U.S. PATENT DOCUMENTS

| | | | | |
|---|---|---|---|---|
| 5,473,934 A | * | 12/1995 | Cobb | 73/61.49 |
| 5,610,611 A | | 3/1997 | McEwan | 342/89 |
| 5,717,337 A | * | 2/1998 | Kelly | 324/534 |
| 6,441,622 B1 | * | 8/2002 | Wrzesinski et al. | 324/643 |
| 6,477,474 B1 | | 11/2002 | Diede | 702/57 |
| 6,657,443 B1 | * | 12/2003 | Anderson | 324/664 |
| 6,707,307 B1 | * | 3/2004 | McFarlane et al. | 324/664 |
| 6,782,328 B1 | * | 8/2004 | Lovegren et al. | 702/50 |
| 6,798,215 B1 | * | 9/2004 | DeHart | 324/640 |
| 6,831,468 B1 | * | 12/2004 | Anderson et al. | 324/664 |
| 2002/0177961 A1 | * | 11/2002 | Lovegren et al. | 702/50 |

* cited by examiner

*Primary Examiner*—Diane Lee
*Assistant Examiner*—Marina Kramskaya
(74) *Attorney, Agent, or Firm*—Klaus J. Bach

(57) ABSTRACT

In a method and apparatus for determining the moisture content of a material with a measuring line extending through the material and having a proximal end connected to a signal generator for supplying a pulse signal to the measuring line, which pulse signal is reflected and returned back to the proximal end of the measuring line to which a comparator is connected for measuring the travel time of the signal supplied, and the reflected signal returned, to the proximal end of the measuring line and its amplitude is with compared with an amplitude corresponding to a threshold, an adjustable threshold value generator and controller are provided generating a threshold value signal which depends on the amplitude of the reflected signal.

9 Claims, 3 Drawing Sheets

METHOD AND APPARATUS FOR DETERMINING THE MOISTURE CONTENT OF A MATERIAL

BACKGROUND OF THE INVENTION

The invention relates to a method and apparatus for determining the moisture content of a material by way of measuring the dielectric constant of the material, wherein a pulsed signal is applied to a proximate end of a measuring line extending through the material and is reflected at the distal end of the measuring line and the reflected signal is detected at the proximate end and compared with a threshold value and also the time delay between the signal application and the return of the reflected signal is evaluated.

Such a method and apparatus is disclosed for example in EP 0 478 815, which is assigned to the assignee of the present application and is marketed by the Assignee with considerable success. In this known method, a square signal is applied to a measuring cable. The pulse direction of the signal is greater than twice the travel time of the signal in the measuring cable. At the input of the measuring cable or, respectively, the output of the measuring signal generator the respective amplitudes are therefore superimposed thereby generating a summing signal formed by the input signal and the signal reflected from the distal end of the cable.

Although this known method provides very good results, it does have the disadvantage that the amplitude of the reflected signal affects the measuring accuracy. This is disturbing since the amplitude of the reflected signal depends on the electric conductivity and, consequently, the moisture content of the material. Furthermore, the ambient temperature around the measuring cable affects the amplitude of the reflected signal.

U.S. Pat. No. 6,477,474 B2 discloses a method for determining the dielectric constant of a material wherein, by means of an impulse generator, a pulse signal is supplied to a measuring cable and the travel time up to the reception of the reflected signal is determined and the dielectric constant is determined therefrom. A threshold value control circuit is provided by which a threshold value can be adjusted to a fixed threshold value or it can be adjusted depending on the reflected signal. However, definite criteria for the adjustment of the threshold value are not available from this publication.

Furthermore, U.S. Pat. No. 5,610,611 discloses an impulse reflectometer wherein an automatic threshold value adjustment occurs depending on the size of the reflected signal.

It is the object of the present invention to provide a method and apparatus for determining the moisture content of a material by which the accuracy of the measurement is improved.

SUMMARY OF THE INVENTION

In a method and apparatus for determining the moisture content of a material with a measuring line extending through the material and having a proximal end connected to a signal generator for supplying a pulse signal to the measuring line, which pulse signal is reflected and returned back to the proximal end of the measuring line to which a comparator is connected for measuring the travel time of the signal supplied, and the reflected signal returned, to the proximal end of the measuring line and its amplitude is with compared with an amplitude corresponding to a threshold, an adjustable threshold value generator and controller are provided generating a threshold value signal which depends on the amplitude of the reflected signal.

It has been recognized that, upon arrival of the reflected signal at the proximal end of the measuring line or, respectively, the output of a corresponding signal generator, the voltage does not increase vertically but that the voltage increase of the summing signal formed from the signal supplied to the measuring line and the signal reflected from the distal end of the measuring line occurs within a certain time period which must not be neglected. The rate of increase of voltage depends on the height of the amplitude of the reflected signal. With a high amplitude, the voltage slope is steeper so that the threshold value of the comparator is reached more rapidly. Consequently, with a fixed threshold value, the point in time of switching of the comparator, that is the measured point in time of return of the reflected signal depends on the height of the amplitude of the reflected signal.

If, with a predetermined amplitude of the reflected signal, the level of the threshold value corresponds to about 80% of the amplitude of the reflected signal (over to the amplitude of the input signal), the comparator switches at a certain point in time. If the amplitude of the reflected signal changes, for example under the influence of the temperature or moisture, the level of the threshold value is no longer 80% of the amplitude of the reflected signal (over the amplitude of the input signal). The comparator then switches at a different point in time. This is disadvantageous: It introduces some inaccuracy, since the point in time of switching should depend only on the travel time of the signal.

As the threshold value is adjustable depending on the amplitude of the reflected signal, the point of switching of the comparator can be adapted advantageously to the reflected signal. Differences in the size of the amplitude of the reflected signal can be equalized wherein it is of no importance on the basis of which disturbing influences the amplitude of the reflected signal has changed. As a result, in a highly advantageous manner, also influences caused by temperature variations of the material of the measuring line and the evaluation device are almost completely eliminated. The time of switching of the comparator depends only on the travel time of the signal which, with a travel time measurement, has a substantial influence on the accuracy.

It has been found to be highly advantageous to determine the voltage change of the signal generator, that is, the slope of the voltage change for forming the threshold value. It has been found that the measuring accuracy is highest if the switching time of the comparator is always at a point where the slope of the voltage change of the summing signal over time has always the same predetermined inclination.

In this connection, it is very advantageous if the threshold value of the comparator corresponds to the voltage of the summing signal determined from the input signal and the reflected signal at which the voltage change of the summing signal is about one third to two thirds, particularly two fifths to four fifths and preferably one half of the average of the inclination of the increasing flank of the signal supplied to the measuring line. The average inclination of the increasing flank of the voltage of the signal supplied to the measuring line is formed from the difference between 90% of the amplitude of the input signal and 10% of the amplitude of the input signal and the associated points in time.

It is in this connection very advantageous to form the threshold value from the sum of the amplitude of the input signal and a fraction of the amplitude of the reflected signal as it is provided for in a particular embodiment of the invention. It has been found to be very advantageous if the fraction of the amplitude of the reflected signal is about 50 to 95%, particularly 65 to 85% and preferably 75%.

Since for forming the threshold value, a fraction of the amplitude of the reflected signal is used, the point in time of switching of the comparator is always about in the same area of the flank of the voltage change at the proximal end of the measuring line or, respectively, the output of the signal generator. This is very advantageous with regard to the accuracy of the measuring results.

For determining the rate of the voltage change over time, first, an empirically determined threshold value can be set. With this threshold value, a first measurement is performed. The travel time of the signal up to the return of the reflected signal at the proximal end of the measuring line determined in this way or, respectively, the second point in time determined in this way is recorded as the first measuring value. Then the threshold value can be slightly increased and a second measurement performed. The difference between the two measured times is divided by the difference between the two threshold values.

In this way, the inverse value of the slope or the amplitude change over time is obtained. If a comparison with a predetermined value shows that the slope is too large, the procedure is repeated with higher threshold values. If the slope is too small, a lower threshold value is used. The threshold values are changed until the slope is within the tolerance limits for the predetermined value.

With the threshold value determined in this way, it is ensured that the point in time of switching of the comparator is always in the same area of the curve showing the voltage change over time independently of whether the reflected signal has a large amplitude or a small amplitude. A range has been found to be very advantageous in which the reflected signal has reached about 75% of its amplitude top.

Very good measuring results were obtained with an inverse value of the quotient of about 3 nanoseconds per volt to 8 nanoseconds per volt, particularly 4 nanoseconds per volt to 6 nanoseconds per volt and preferably 5 nanoseconds per volt.

In another embodiment of the invention, a reference line is provided to the proximal end of which a pulsed signal is supplied. A second comparator is present which at the proximal end of the reference line receives the signal reflected at the distal end of the line and compares the reflected signal with a reference threshold value.

Since the signals are supplied to the reference line by a separate signal generator, the internal resistance of the signal generator for the measuring line is smaller which is advantageous with respect to the accuracy of the measurement. Furthermore, the reference line and the signal line are completely uncoupled so that they do not influence each other. Also, the respective circuit components with an ASIC can be spatially separated whereby a very good HF uncoupling is achieved.

Further details, features, and advantages of the invention will become more readily apparent from the following description of a particular embodiment thereof described below with reference to the accompanying drawings.

DESCRIPTION OF PREFERRED EMBODIMENTS

Figure 1:
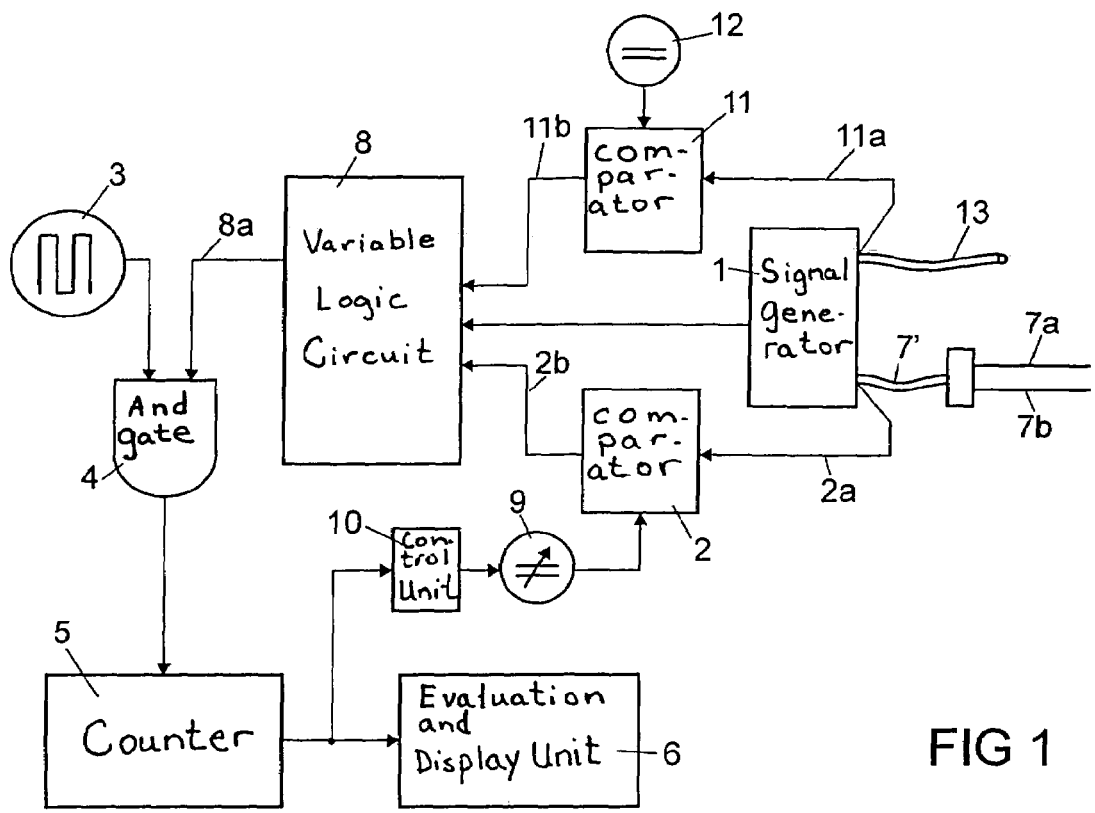
FIG. 1 shows an arrangement for performing the method according to the invention.

As shown in FIG. 1, a measuring line 7a, 7b is connected to a signal generator 1 by way of a connecting line 7'. The output of the signal generator 1 or, respectively, the proximal end of the measuring line 7a, 7b is connected to a first input of a first comparator 2. A second input of the first comparator 2 is connected to an output of an adjustable threshold value generator 9. The output of the first comparator 2 is connected to a variable logic circuit 8. Furthermore, a control output of the signal generator 1 is connected to the variable logic circuit 8.

The signal generator 1 is further connected to the proximal end of a reference line 13. The respective output of the signal generator 1 or, respectively, the proximal end of the reference line 13 is connected to the input of a second comparator 11. A second input of the second comparator 11 is connected to a reference threshold value generator 12. The output of the second comparator 11 is connected to the variable logic circuit 8. The output of the variable logic circuit 8 is connected to an input of an AND gate 4. A second input of the AND gate 4 is connected to an oscillator 3. An output of the AND gate 4 is connected to the counter 5. The output of the counter 5 is connected to a control unit 10 and to an evaluation and display unit 6. The output of the control unit 10 is connected to a control input of the variable threshold value generator 9.

The operation of the arrangement will be described below on the basis of the voltage curve shown in FIG. 3, which was recorded at the output of the signal generator 1 or respectively the input of the connecting line 7'.

First a measuring signal is supplied by the signal generator 1 to the connecting line 7'. The measuring signal has the same pattern as shown by the first increase of the voltage curve given in FIG. 3. At the time $t_0$, the signal increase begins. At the time $t_0'$ 10% ($U_0'$) of the maximum amplitude of square signal has been reached. At the time $t_0''$ 90% ($U_0''$) of the maximum amplitude ($U_s$) has been reached. After reaching the maximum amplitude ($U_s$), the voltage level of the output signal of the signal generator 1 remains constant for the duration of the travel time measuring period.

Figure 3:
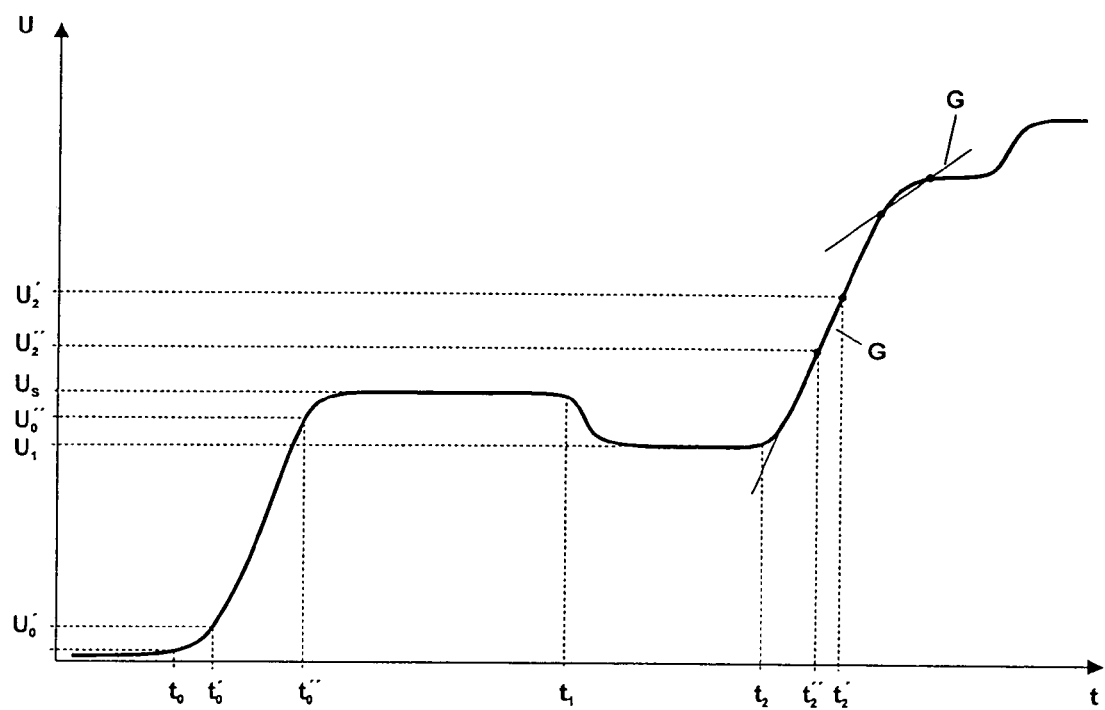
FIG. 3 shows a voltage curve for a signal entering the measuring line.

In the voltage curve as shown in FIG. 3, the signal supplied to the connecting line 7' is reflected upon transition from the connecting line 7' to the measuring line 7a, 7b with a negative amplitude. The reflected signal arrives at the output of the signal generator 1 at the time $t_1$ whereby the voltage of the summing signal present at the output of the signal generator is slightly reduced ($U_1$).

Corresponding to the moisture content of a particular material to be examined, the signal is delayed in the measuring line 7a, 7b and at the end of the measuring line 7a, 7b, is reflected time-delayed with a positive amplitude. The reflected signal arrives about at the time $t_2$ at the output of the signal generator 1. Since the flank of the summing signal formed at the output of the signal generator 1 is not exactly vertical, the time at which the reflected signal arrives can be determined generally only quite inaccurately, particularly since the amplitude of the reflected signal depends on the electric conductivity and therefore the moisture content of the material.

At the point in time of arrival of the reflected signal is determined in accordance with the invention when the summing signal obtained at the output of the signal generator 1 corresponds to a threshold value which is adjusted depending on the amplitude of the reflected signal. For determining the threshold value a first search threshold value $U_2'$ which corresponds about to the amplitude of the measuring signal ($U_s$) supplied by the signal generator 1 to the connecting line 7' plus 40% of the amplitude of the signal reflected in the measuring line 7a, 7b is first provided at a first comparator 2 by means of the control device 10 and the threshold value generator 9. With this first search threshold value $U_2'$, a first travel time measurement is performed wherein the voltage of the signal value at the time $t_2'$ obtained at the output of the signal generator 1 corresponds to the first search threshold value $U_2'$.

Upon arrival of the signal reflected in the measuring line 7a, 7b at the respective output of the signal generator 1 or, respectively, at the input of the first comparator 2, the signal present at the input of the first comparator 2 exceeds the threshold value present at the second input of the first comparator 2. As a result, the signal 2b present at the output of the first comparator 2, which up to this point was positive, becomes zero (see FIG. 4b).

At the same time, when the measuring signal is applied by the signal generator 1 to the reference line 13. The measuring signal is reflected in the reference line 13 with a positive amplitude. After the signal reflected in the reference line has arrived at the respective output of the second comparator 11, the signal 11a present at the input of the second comparator 11 exceeds the reference threshold value present at the second input of the second comparator 11. As a result, the signal 11b provided at the output of the second comparator 11, which so far was positive, becomes zer0 (see FIG. 4a). In the variable logic circuit 8 the output signal 11b of the second comparator 11 is combined with the output signal 2b of the first comparator 2 in such a way that the signal 8a provided at the output of the logic circuit 8 at the time when the second comparator switches, becomes positive and becomes again zero when the first comparator 2 switches (see FIG. 4c).

At the output of the AND gate 4, there are consequently the impulses of the oscillator 3 present during the time between the arrival of the signal reflected in the reference line 13 and the arrival of the signal reflected in the measuring line 7a, 7b. These impulses are counted in the counter 5. The count value represents a measure for the travel time of the measuring signal in the measuring line 7a, 7b and is a measure for the moisture content of the material in which the measuring line 7a, 7b is disposed. The output value of the counter 5 is provided to the display unit 6.

Furthermore, the output value of the counter 5 is applied to the control device 10 which adjusts the threshold value generator 9. With the first travel time measurement, the first search threshold value is obtained.

After completion of the first travel time measurement, at the first comparator 2 a second search threshold value $U_2''$ is set which corresponds to the value of the amplitude of the measuring signal supplied by the signal generator 1 to the connecting line 7' plus twenty five % of the amplitude of the signal reflected in the measuring line 7a, 7b. For forming the second search threshold value $U_2''$, the first search threshold value $U_2'$ was consequently reduced by fifteen percent of the amplitude of the signal reflected in the measuring line 7a, 7b. With the second search threshold value $U_2''$, a second travel time measurement is performed, wherein the voltage of the signal present at the output of the signal generator 1 at the point in time $t_2''$ corresponds to the second search threshold value $U_2''$. By means of two measurement values obtained in this way, the inclination of a straight line G is calculated which is defined by the two measurement values $U_2',t_2/U_2''$, $t_2''$ of the voltage curve of the summing signal present at the output of the signal generator 1.

If the inclination or slope of the straight line G has less than a predetermined value, the measuring cycle described above is repeated with new first and second search threshold values wherein the new first search threshold value is selected so as to be sixteen percent of the amplitude of the signal reflected in the measuring line 7a, 7b below the search threshold value selected in the previous measuring cycle. The new first search threshold value of the second measuring cycle therefore corresponds to the amplitude of the measuring signal supplied to the connecting line 7' plus twenty four percent of the amplitude of the signal reflected in the measuring line 7a, 7b. The new second search threshold valve is again by fifteen percent of the amplitude of the signal reflected in the measuring line 7a, 7b lower than the new first search threshold value. By way of the new travel time measurements obtained with the two new actual search threshold values the slope of a straight line is again determined which is defined by the two points determined by the two measurement values of the summing signal at the output of the signal generator 1.

If the slope obtained in this way is still smaller than the predetermined slope a third measurement cycle is performed, wherein the first search threshold value is again reduced by sixteen percent of the amplitude of the signal reflected in the measuring line 7a, 7b. The measuring cycle is repeated with a search threshold value reduced by sixteen percent of the amplitude of the signal reflected in the measuring line 7a, 7b, until the calculated slope of the straight line defined by the two points determined by the two measurement values is greater than the predetermined slope.

When the calculated slope is greater than the predetermined slope, that is, when in the comparison the sign is reversed, the last first search threshold value is increased by one half of the reduction which was previously employed up to the sign reversal that is, in the present case by ½ of sixteen %, that is 8% of the amplitude of the signal reflected in the measuring line 7a, 7b and a new measuring cycle is performed.

Generally, it can be said: As long as a comparison does not result in a sign reversal, the first search threshold value is changed by the same amount by which it was changed in the previous measuring cycle. When the comparison shows a sign reversal, the search threshold value is changed by half the amount by which it was changed in the preceding measurement cycle and in the opposite sense. The second search threshold value is always by fifteen percent of the amplitude of the signal reflected in the measurement line 7a, 7b smaller than the first search threshold value.

The iterative approximation to the predetermined slope as described above is performed until the first search threshold value has been changed by only one percent of the amplitude of the signal reflected on the measuring line 7a, 7b and a new change with reversed sign would be necessary.

The first search threshold value determined in this way is then finally reduced by twenty percent of the amplitude of the signal reflected in the measuring line 7a, 7b. This value then forms the threshold value on the basis of which the moisture content of the material is determined.

By means of the reference line 13 and the second comparator 11 provided therefor, the start of the travel time measurement can be changed in an advantageous way. The travel time measurement may be started for example only when the signal reflected in the reference line 13 arrives at the output of the signal generator 1. In this way, a change of the voltage curve caused particularly by a reflection with negative amplitude can be eliminated at the output of the signal generator 1 as it is apparent from FIGS. 4a to 4c.

Figure 4A:
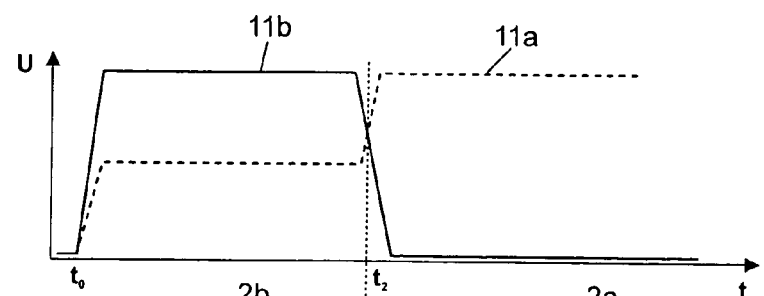
FIG. 4a to FIG. 4c show idealized signal curves with a reflection having a negative amplitude and a reflection having a positive amplitude in the signal line.
Figure 4B:
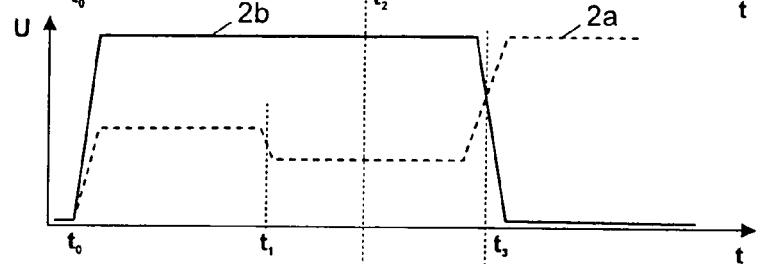
Figure 4C:
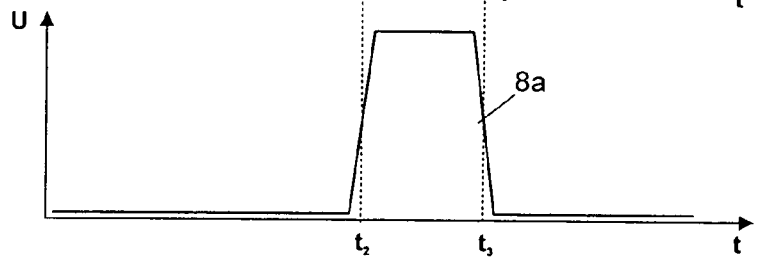

In FIG. 4a, the signal values 11a obtained at the input of the reference line 13 or respectively at the corresponding output of the signal generator 1, which are also present at the input of the second comparator 11 and the signal values 11b present at the output of the second comparator 11 are schematically shown. FIG. 4b shows the signal values 2a present at the input of the connecting line 7' or, respectively, the corresponding output of the signal generator 1, which are also present at the input of the first comparator 2, as well as the signal values 2b present at the output of the first comparator 2. FIG. 4c shows schematically the signal values 8a present at the output of the logic circuit 8.

As shown in FIGS. 4a and 4b, a reference signal is supplied to the reference line 13 at the time $t_0$ when a measuring signal is supplied to the connecting line 7'. The signal reflected in the reference line 13 arrives at the output of the signal generator 1 at the time $t_2$. As a result, the second comparator 11 switches. The signal 11b present until then at the output of the second comparator 11 then becomes zero. In this way, the output signal 8a of the logic circuit becomes positive as shown in FIG. 4c. With the positive output signal 8a of the logic circuit 8, the travel time measurement is started at the time $t_2$.

When at the time $t_3$, the signal reflected in the measuring line 7a, 7b arrives at the respective output of the signal generator 1 with a positive amplitude, the first comparator 2 switches. The signal 2b present until then at the output of the first comparator 2 then becomes zero. As a result, the output signal 8a of the logic circuit 8 becomes zero whereby the travel time measurement is ended.

The travel time is therefore measured only between the time points $T_2$ and $t_3$ as apparent from FIG. 4c. Disturbances arriving with a negative reflection at the time $t_1$ as shown in FIG. 4b have therefore no effect.

Figure 5A:
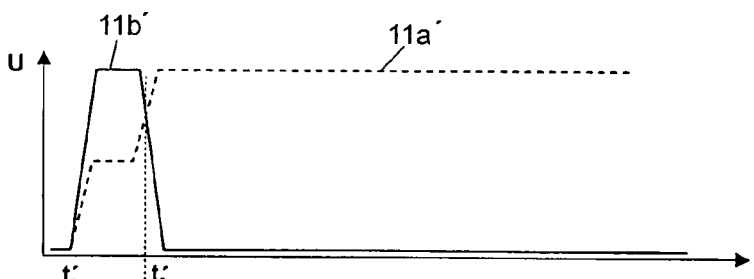
FIGS. 5a to 5c show idealized signal curves with a reflection with negative amplitude on the signal line.
Figure 5B:
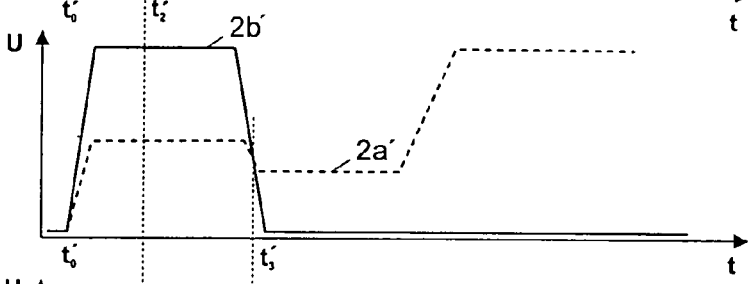
Figure 5C:
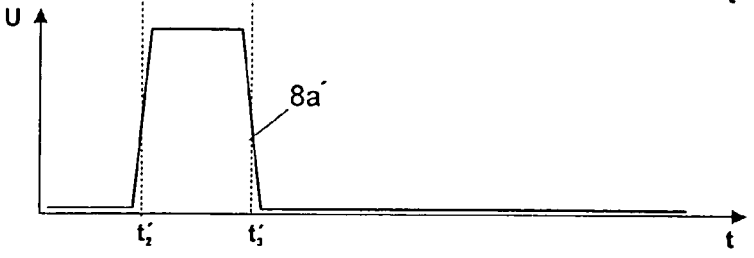

FIG. 5 shows schematically the signal values 11a' which are present at the output of the reference line 13, or at the respective output of the signal generator 1 and also at the input of the second comparator 11 and the signal values 11b' present at the output of the second comparator 11. FIG. 5b shows the signal values 2a', which are present at the input of the connecting line 7 or the respective output of the signal generator 1 and also at the input of the first comparator 2 and the signal values 2b' present at the output of the first comparator 2. FIG. 5c shows schematically the signal values 8a' present at the output of the logic circuit 8.

As shown in FIGS. 5a to 5c, the reference line 13 may also be so selected that the signal reflected in the reference line 13 arrives at the respective output of the signal generator 1 already when the signal reflected at the transition from the connecting line 7' to the measuring line 7a, 7b with negative amplitude has not yet arrived at the respective output of the signal generator 1. Consequently, the travel time measurement can be started at a time $t_2'$ when the signal 2a' supplied to the connecting line 7' or, respectively, the measurement line 7a, 7b has reached the maximum amplitude. In this way, a threshold value can be set at the first comparator 2, which is below the amplitude of the measuring signal supplied to the connecting line 7'. This has the advantage that a reflection with a negative amplitude can be measured.

As a result, the arrangement according to the invention can be used for measuring filling degrees. It has been found that if the measuring line 7a, 7b is for example partially immersed into a liquid a reflection with negative amplitude occurs at the surface of the liquid.

Figure 2:
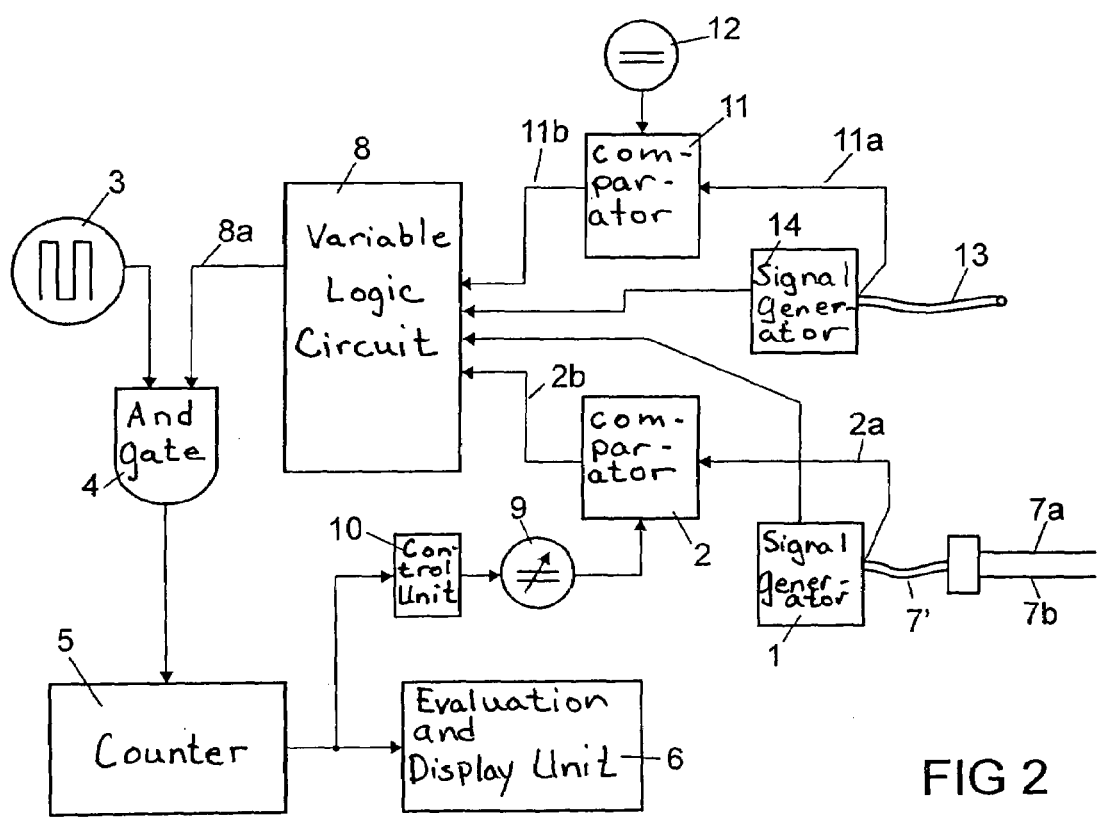
FIG. 2 shows another arrangement for performing the method according to the invention.

In the embodiment shown in FIG. 2, a separate signal generator 14 is provided for the reference line 13. Otherwise the embodiment of FIG. 2 is essentially the same as that shown in FIG. 1. Identical elements are therefore indicated by the same reference numerals.

Because of the separate signal generator 14 for the reference line 13, the internal resistance of the signal generator 1 may be lower which is advantageous with regard to the measurement accuracy. Furthermore, there is no feedback from reference line 13 to the measuring line 7a, 7b, which is also advantageous with respect to the measuring accuracy. In addition, the respective circuit parts can be spatially separate whereby a good HF uncoupling can be achieved.

What is claimed is:

1. A method for determining the moisture content of a material with a measuring line extending through the material and having a proximal end and a distal end spaced from the proximal end, said method comprising the steps of: applying a pulsed signal to the proximal end of the measuring line which is reflected at a distance from the proximal end of the measuring line, forming a threshold value from the amplitude of a summing signal generated by the signal supplied to the measuring line and the reflected signal wherein the slope of the voltage change of the summing signal corresponds to one third to two thirds of the average inclination of the increasing flank of the signal applied to the measuring line, detecting the reflected signal at the proximal end of the measuring line and comparing it with the threshold value, determining the travel time up to the return of the reflected signal at the proximal end of the measuring line which is detected when the signal at the proximal end exceeds the threshold value, evaluating the travel time and adjusting the threshold value based on the change of the amplitude per time unit of the reflected signals at the proximal end of the measuring line, whereby the moisture content is determined on the basis of the threshold value, and displaying the moisture content on a display unit.

2. A method according to claim 1, wherein the threshold value is formed from the sum of the amplitude of the signal supplied to the measuring line and a fraction of the amplitude of the reflected signal.

3. A method according to claim 2, wherein the fraction of the reflected signal is between 50 and 95 percent.

4. A method according to claim 3, wherein the fraction of the reflected signal is about 75%.

5. A method according to claim 1, wherein the voltage change of the summing signal corresponds to about one half of the average inclination of the increasing flank of the signal supplied to the measuring line.

6. An arrangement for determining the moisture content of a material, comprising a measuring line (7a, 7b) extending through the material and having a proximal end and a distal end, a signal generator (1) connected to the proximal end of the measuring line (7a, 7b) for supplying a pulsed signal thereto, a comparator (2) connected to the proximal end of the measuring line (7a, 7b) for receiving a signal reflected from the measuring line (7a, 7b) back to the proximal end thereof and comparing it with a threshold value, a device (3, 4, 5, 8) for measuring a first period between a first point in time when the signal is supplied to the proximal end of the measuring line (7a, 7b) and a second point in time when the reflected signal returned from the measuring line (7a, 7b) has an amplitude corresponding to a certain threshold value, an adjustable threshold value generator (9) and a controller (10) for generating an output signal depending on the amplitude of the reflected signal in such a way that the quotient of the difference between two threshold values and the difference between the respective second points in time wherein the amplitudes of the reflected signals correspond to the respective threshold value is formed and compared with a predetermined value, a reference line (13) having a proximal end and a distal end provided in said material, and a second comparator (11) connected to the proximal end of the reference line (13) such that a pulsed signal supplied to the proximal end of the reference line (13) and reflected at the distal end is received by the second comparator and compared therein with a reference threshold value.

7. An arrangement according to claim 6, wherein the inverse value of the predetermined value is between 3 nanoseconds per volt and 8 nanoseconds per volt.

8. An arrangement according to claim 7, wherein the inverse value of the predetermined value is about 5 nanoseconds per volt.

9. An arrangement according to claim 6, wherein a second signal generator (14) is provided for supplying the pulsed signal to the proximal end of the reference line (13).

\* \* \* \* \*